United States Patent
Domínguez Rodríguez et al.

(10) Patent No.: US 10,278,956 B1
(45) Date of Patent: May 7, 2019

(54) USE OF INTRAVENOUS MELATONIN IN PATIENTS WITH ST-ELEVATION MYOCARDIAL INFARCTION

(71) Applicants: Alberto Domínguez Rodríguez, Santa Cruz de Tenerife (ES); Pedro Abreu González, Santa Cruz de Tenerife (ES)

(72) Inventors: Alberto Domínguez Rodríguez, Santa Cruz de Tenerife (ES); Pedro Abreu González, Santa Cruz de Tenerife (ES)

(73) Assignees: Alberto Domínguez Rodríguez, Santa Cruz de Tenerife (ES); Pedro Abreu González, Santa Cruz de Tenerife (ES)

( * ) Notice: Subject to any disclaimer, the term of this patent is extended or adjusted under 35 U.S.C. 154(b) by 0 days.

(21) Appl. No.: 15/922,335

(22) Filed: Mar. 15, 2018

(51) Int. Cl.
*A61K 31/4045* (2006.01)
*A61P 9/10* (2006.01)
*A61K 9/00* (2006.01)
*A61M 25/10* (2013.01)

(52) U.S. Cl.
CPC ........ *A61K 31/4045* (2013.01); *A61K 9/0019* (2013.01); *A61P 9/10* (2018.01); *A61M 25/104* (2013.01)

(58) Field of Classification Search
None
See application file for complete search history.

(56) References Cited

PUBLICATIONS

Dominguez-Rodriguez et al. "Usefulness of Early Treatment With Melatonin to Reduce Infarct Size in Patients With ST-Segment Elevation Myocardial Infarction Receiving Percutaneous Coronary Intervention . . . ", Aug. 15, 2017; ePub May 20, 2017, American Journal of Cardiology, vol. 120, pp. 522-526 (Year: 2017).*

Dominguez-Rodriguez, Alberto, et al.; "Effect of intravenous and intracoronary melatonin as an adjunct to primary percutaneous coronary intervention for acute ST-elevation myocardial infarction: Results of the Melatonin Adjunct in the acute myocaRdial Infarction treated with Angioplasty trial," J. Pineal Res., 2017, https://doi.org/10.1111/ipi.12374, vol. 62 (1), pp. 1-9, Jan. 2017.

Ekeløf, Sara V., et al.; "Effects of intracoronary melatonin on ischemia-reperfusion injury in ST-elevation myocardial infarction," Heart Vessels, 2014, DOI 10.1007/s00380-014-0589-1.

Dominguez-Rodriguez, Alberto, et al.; "A unicenter, randomized, double-blind, parallel-group, placebo-controlled study of Melatonin as an Adjunct in patients with acute myocandial Infarction undergoing primary Angioplasty the Melatonin Adjunct in the acute myocandial Infarction treated with Angioplasty (MARIA) trial: Study design and rationale," Contemporary Clinical Trials, 2007, pp. 532-539, vol. 28.

Dominguez-Rodriguez, Alberto, et al.; "Time to Treatment with Melatonin and Infarct Size in Patients with St-Segment Elevation Myocardial InfarctionL Insights from the Maria (Melatonin Adjunct in the Acute Myocardial Infarction Treated with Angioplasty) Trial," JACC, 2017, vol. 69, Issue 11, Presentation No. 1242-162.

Dominguez-Rodriguez, Alberto, et al.; Usefulness of Early Treatment With Melatonin to Reduce Infarct Size in Patients With ST-Segment Elevation Myocardial Infarction Receiving Percutaneous Coronary Intervention (From the Melatonin Adjunct in the Acute Myocardial Infarction Treated With Angioplasty Trial), Am J Cardiol, 2017, http://dx.doi.org/10.1016/j.amjcard.2017.05.018, vol. 120, pp. 522-526.

* cited by examiner

*Primary Examiner* — Brandon J Fetterolf
*Assistant Examiner* — Gregg Polansky
(74) *Attorney, Agent, or Firm* — Tristan A. Fuierer; Olive Law Group, PLLC

(57) ABSTRACT

The invention relates to a method of treating a subject who has suffered a myocardial infarction with ST-elevation and to a method of treating reperfusion injury in a subject, the method comprising intravenous administration of melatonin to the subject, wherein the administration is initiated within 3 hours or less of symptom onset and prior to the mechanical reperfusion and is maintained for at least 60 minutes.

20 Claims, No Drawings

USE OF INTRAVENOUS MELATONIN IN PATIENTS WITH ST-ELEVATION MYOCARDIAL INFARCTION

FIELD OF THE INVENTION

The invention relates to the intravenous administration of melatonin to a subject with ST-elevation myocardial infarction treated with percutaneous coronary intervention.

BACKGROUND OF THE INVENTION

Acute myocardial infarction is a major cause of mortality and disability worldwide. In patients with myocardial infarction, the treatment option for reducing acute myocardial ischemic injury and limiting myocardial infarction size is timely and effective myocardial reperfusion using either thrombolytic therapy or primary percutaneous coronary intervention (pPCI).

Although reperfusion therapy during acute myocardial infarction with percutaneous coronary intervention (PCI) or thrombolysis salvages myocardium that would ultimately die without reperfusion, rapidly restoring blood flow to myocardium can also cause lethal injury to vulnerable myocardial cells (i.e., reperfusion injury). The restoration of blood flow can lethally compromise oxygen-deprived cells. Reperfusion injury may offset the optimal salvage of myocardium achieved by PCI and/or thrombolysis. Over the last 20 years extensive research efforts have been devoted to develop therapeutic strategies to prevent reperfusion injury.

There is still a need for additional methods for the treatment of cardiac and cardiovascular disorders and myocardial reperfusion injury by limiting infarct-size through post-ischemia reperfusion injury.

Due to its antioxidant and free-radical scavenger properties, the use of melatonin in the treatment of myocardial infarction has been hypothesized (e.g. A. Dominguez-Rodriguez et al. Contemporary Clinical Trials 2007, 532-539). However, in a clinical proof-of-concept trial, A. Dominguez-Rodriguez et al. (J. Pineal Res. 2017, 62: e12374) found that melatonin failed to reduce myocardial infarct size (MIS) compared with placebo and had an unfavorable effect on the ventricular volumes and LVEF evolution among patients with ST-segment elevation myocardial infarction (STEMI).

Similarly, Ekeløf et al. (Heart Vessels 2016, 31(1), 88-95) found that combined intracoronary and intravenous treatment with melatonin did not reduce myocardial reperfusion injury in a closed-chest porcine model.

Infarct size is a major predictor of post-STEMI mortality and morbidity, and there is still a need for adjunct therapies to PCI that reduce the extent of myocardial damage associated with reperfusion.

DESCRIPTION OF THE INVENTION

Timely reperfusion salvages myocardium from tissue injury after prolonged ischemia. However, restoration of blood flow to ischemic myocardium may exaggerate injury that is not present at the end of ischemia. This reperfusion injury is primarily expressed as contractile and coronary vascular endothelial dysfunction, upregulation of adhesion molecules on the endothelium, and transendothelial migration of inflammatory cells into the parenchyma, edema, infarction, and apoptosis. There is still no effective therapy for myocardial reperfusion injury. Embodiments of the present invention provide methods for treating this reperfusion injury as well as for reducing myocardial infarct size.

Despite previously disclosed negative results in relation to the use of melatonin to reduce myocardial infect size, the inventors have surprisingly found that early after symptom onset intravenous administration of melatonin in patients with ST-elevation myocardial infarction (STEMI) is associated with a significant reduction in the infarct size after percutaneous coronary intervention (PCI). In particular, the inventors found that intravenous administration of melatonin given within 3 hours or less after symptom onset and starting short before PCI significantly reduces myocardial infarct size in STEMI-patients compared with placebo. In contrast, a significantly reduced or even opposite effect was observed when the time from symptom onset to melatonin administration is longer.

These results suggest that early administration of melatonin results in a significant cardioprotective effect against ischemia-reperfusion. This finding has important clinical implications for the treatment of patients with STEMI.

Importantly, the inventors have found that intracoronary administration of melatonin is not required and the cardioprotection is observed even if melatonin is administered only intravenously.

Melatonin can thus be used as an adjunct treatment in acute myocardial infarction treated with mechanical reperfusion.

Therefore, a first aspect of the invention is directed to a method of treating a subject who has suffered a myocardial infarction with ST-elevation and with total occlusion of the infarct-related artery (TIMI flow grade 0-1), the method comprising intravenous administration of melatonin and mechanical reperfusion, wherein the administration is initiated within 3 hours or less of symptom onset and prior to the mechanical reperfusion and is maintained for at least 60 minutes.

In another aspect, the invention is directed to a method of treating reperfusion injury due to mechanical reperfusion in a subject suffering ST-elevation myocardial infarction with total occlusion of the infarct-related artery (TIMI flow grade 0-1), the method comprising intravenous administration of melatonin to the subject, wherein the administration is initiated within 3 hours or less of symptom onset and prior to the primary percutaneous coronary intervention and is maintained for at least 60 minutes.

Melatonin as used herein includes pharmaceutically acceptable salts, solvates and prodrugs thereof. Preferably, melatonin is used in its free form.

As used in relation to the invention, the term "treating" or "treatment" and the like should be taken broadly. They should not be taken to imply that a subject is treated to total recovery. Accordingly, these terms include amelioration of the symptoms or severity of a particular condition or preventing or otherwise reducing the risk of further development of a particular condition.

The term "ST-elevation myocardial infarction" according to the invention refers to ST elevation at J-point in two contiguous leads with cut-off points $\geq 0.2$ mV in men or $\geq 0.15$ mV in women in leads V2-V3 and/or $\geq 0.1$ mV in other leads.

The Thrombolysis In Myocardial Infarction (TIMI) flow grade classification scheme is widely used to assess coronary artery perfusion beyond point of occlusion on coronary angiography. TIMI flow grade 0 refers for no antegrade flow beyond the point of occlusion. TIMI flow grade 1 refers for faint antegrade coronary flow beyond the occlusion with incomplete filling of the distal coronary bed.

It should be appreciated that methods of the invention may be applicable to various species of subjects, preferably mammals, more preferably humans.

Particular embodiments of the methods of the present invention are defined below.

In the methods of the present invention, melatonin is administered within the first 3 hours of symptom onset.

The term "myocardial infarction symptom onset" as used herein refers to the time point where the subject presents symptoms characteristic of myocardial infarction such as chest pain, arm pain, abdominal pain, heartburn, shortness of breath, sweating, nausea, vomiting, abnormal heart beating, anxiety, fatigue, weakness and dizziness.

In a particular embodiment, the administration of melatonin is initiated within 170 minutes or less of symptom onset, preferably within 160 minutes or less of symptom onset, more preferably within 150 minutes or less. In an embodiment, the administration of melatonin is initiated from 1, 5, 10 or 15 to 150, 160, 170 or 180 minutes of symptom onset.

In a particular embodiment, the administration of melatonin is initiated within 180 minutes of less of myocardial infarction, preferably within 170 minutes or less of myocardial infarction, more preferably within 160 minutes or less of myocardial infarction, even more preferably within 150 minutes or less of myocardial infarction. In an embodiment, the administration of melatonin is initiated from 1, 5, 10 or 15 to 150, 160 or 180 minutes of myocardial infarction.

Preferably, melatonin is administered prior to and concurrent with the mechanical reperfusion.

In a particular embodiment, the administration of melatonin is initiated within 18 minutes or less prior to the mechanical reperfusion, preferably within 15 minutes or less, more preferably within 10 minutes or less, even more preferably within 5 minutes or less prior to the mechanical reperfusion.

In one embodiment, the administration of melatonin is initiated from 0.5 to 18 minutes prior to the mechanical reperfusion, preferably from 0.5 to 15 minutes, more preferably from 0.5 to 10 minutes, even more preferably from 1 to 5 minutes prior to the mechanical reperfusion.

Mechanical reperfusion includes, for example, percutaneous coronary intervention (PCI), angioplasty and other procedures utilizing an intravascular catheter. Preferably, mechanical reperfusion refers to percutaneous coronary intervention.

Administration of melatonin is maintained for at least 60 minutes from initiation of the administration, preferably for at least 65 minutes, more preferably for at least 70 minutes, even more preferably for at least 75 minutes.

In an embodiment, administration of melatonin is maintained for a period from 60, 65, 70 or 75 minutes to 120, 180, 240 or 300 minutes.

Preferably, administration of melatonin is performed by continuous perfusion.

According to the methods of the present invention, melatonin is administered at a therapeutically effective amount.

The term "therapeutically effective amount" as used herein refers to the amount of melatonin sufficient to achieve the intended purpose, such as, in this case, treatment of reperfusion injury in the myocardial infarction.

In a particular embodiment, melatonin is administered at a total dose of at least 5, 6, 7, 8, 9, 10, 11 or 12 mg. In an embodiment, melatonin is administered at a total dose of from 5, 6, 7, 8, 9, 10, 11 or 12 mg to 25, 50, 75 or 100 mg.

In an embodiment, melatonin is administered at a total dose of from 8 to 100 mg, preferably from 8 to 50 mg.

In another embodiment, melatonin is administered at a total dose of at least 60, 80, 100, 120, 130, 140 or 150 µg/kg (µg per kg of subject weight). In an embodiment, melatonin is administered at a total dose of from 60, 80, 100, 120, 130, 140 or 150 µg/kg to 300, 500, 1000, 1500 µg/kg. In an embodiment, melatonin is administered at a total dose of from 100 to 1500 µg/kg, preferably from 120 to 1000 µg/kg.

Preferably, melatonin is administered as an isotonic and sterile solution. In a particular embodiment, it is administered in saline solution preferably at a concentration between 200 µM and 5000 µM, or between 300 µM and 3000 µM, or between 500 µM and 2000 µM.

In a particular embodiment of the invention, administration of melatonin is initiated within 3 hours or less of symptom onset and within 15 minutes or less prior to the mechanical reperfusion and is maintained for at least 60 minutes.

In another embodiment, administration of melatonin is initiated within 3 hours or less of symptom onset and within 10 minutes or less, or within 5 minutes or less, prior to the mechanical reperfusion and the melatonin administration is maintained for at least 60 minutes.

In a particular embodiment, administration of melatonin to the subject results in a reduced infarct size. That is, the infarct size is reduced compared to the infarct size in a subject who has not been administered melatonin. Preferably, the reduction in infarct size is at least 5%, 10%, 15%, 20%, 25%, 30%, 35%, 40%, 45% or at least 50%. Reduction of the myocardial infarct size can be determined, for instance, by cardiovascular magnetic resonance (CMR).

It should be understood that the scope of the present disclosure includes all the possible combinations of embodiments disclosed herein.

EXAMPLES

Methods

This pilot study is a prospective, randomized, double-blinded, placebo controlled study of consecutive patients admitted with a STEMI. Additional inclusion criteria were presented within 6 hours of chest pain onset and occlusion of culprit artery with TIMI basal flow grade 0 to 1. Patients randomised to intravenous melatonin received a dose of 12 mg (51.7 µmol, in saline solution, in a volume of 50 ml in an opaque syringe) given by a time period of 60 minutes starting immediately before primary percutaneous coronary intervention (pPCI), by via a catheter positioned within a peripheral vein. The control group received a matching intravenous placebo formulation.

Results

A total of 31 patients were enrolled. Groups were well balanced for age, gender, and cardiovascular risk factors. No significant differences were observed between groups concerning baseline clinical and angiographic characteristics. Randomized patients were divided in 2 groups: Group 1 (patients with ischemia duration 3 hours) and Group 2 (patients with ischemia duration >3 hours). Group 1 there had 17 patients (8 treated with melatonin and 9 with placebo) and in the group 2 there were 14 patients (6 treated with melatonin and 8 with placebo).

Myocardial infarct size was calculated as percentage of left ventricular mass by cardiovascular magnetic resonance (CMR). In the group 1, the myocardial infarct size was significantly smaller in the intravenous melatonin-treated subjects compared with placebo (Table).

| CMR parameters[1] | Group 1 (≤3 hours) | | Group 2 (>3 hours) | |
| --- | --- | --- | --- | --- |
| | Intravenous Melatonin | Intravenous Placebo | Intravenous Melatonin | Intravenous Placebo |
| Infarct size (proportion of left ventricular mass) % | 17.71 ± 7.55* | 33.01 ± 5.96 | 20.62 ± 5.37 | 23 ± 9.06 |
| Infarct size (g)[2] | 16.53 ± 7.28* | 32.82 ± 13.2 | 25.69 ± 7.34 | 22.46 ± 6.99 |

[1]Endocardial and epicardial borders were delineated at end systole and end diastole with short-axis views to quantify volumes, function and left ventricle mass. Quantification of the infarcted myocardium was assessed by delineating the enhanced areas in the late enhancement sequences, with five standard deviations above average, obtained from the remote healthy myocardium and normalized by the left ventricular mass.
*$P < 0.01$ vs Placebo.

Clearly, intravenous melatonin given within 3 hours or less after symptom onset reduces myocardial infarct size in STEMI-patients.

The invention claimed is:

1. A method of treating a subject who has suffered a myocardial infarction with ST-elevation and with total occlusion of the infarct-related artery with a TIMI flow grade of 0-1, the method comprising intravenous administration of melatonin and mechanical reperfusion, wherein the melatonin administration is initiated within 3 hours or less of symptom onset and prior to the mechanical reperfusion and is maintained for at least 60 minutes.

2. The method according to claim 1, wherein the administration of melatonin is initiated within 18 minutes or less prior to the mechanical reperfusion.

3. The method according to claim 1, wherein the mechanical reperfusion is primary percutaneous coronary intervention.

4. The method according to claim 1, wherein the administration of melatonin is initiated within 160 minutes or less of symptom onset.

5. The method according to claim 1, wherein melatonin is administered at a total dose of at least 5 mg.

6. The method according to claim 1, wherein melatonin is administered only intravenously.

7. The method according to claim 1, wherein the administration of melatonin is initiated within 3 hours or less of symptom onset and within 15 minutes or less prior to the mechanical reperfusion and is maintained for at least 60 minutes.

8. The method according to claim 1, wherein the administration of melatonin to the subject results in a reduced infarct size.

9. The method according to claim 8, wherein the reduction in infarct size is at least 5%.

10. The method according to claim 1, wherein melatonin is administered by continuous perfusion.

11. A method of reducing reperfusion injury due to mechanical reperfusion in a subject suffering ST-elevation myocardial infarction with total occlusion of the infarct-related artery with a TIMI flow grade of 0-1, the method comprising intravenous administration of melatonin to the subject, wherein the administration is initiated within 3 hours or less of symptom onset and prior to the mechanical reperfusion and is maintained for at least 60 minutes.

12. The method according to claim 11, wherein the administration of melatonin is initiated within 18 minutes or less prior to the mechanical reperfusion.

13. The method according to claim 11, wherein the mechanical reperfusion is primary percutaneous coronary intervention.

14. The method according to claim 11, wherein the administration of melatonin is initiated within 160 minutes or less of symptom onset.

15. The method according to claim 11, wherein melatonin is administered at a total dose of at least 5 mg.

16. The method according to claim 11, wherein melatonin is administered only intravenously.

17. The method according to claim 11, wherein the administration of melatonin is initiated within 3 hours or less of symptom onset and within 15 minutes or less prior to the mechanical reperfusion and is maintained for at least 60 minutes.

18. The method according to claim 1, wherein melatonin is administered by continuous perfusion.

19. The method according to claim 1, wherein melatonin is administered at a total dose of at least 60 μg/kg.

20. The method according to claim 11, wherein melatonin is administered at a total dose of at least 60 μg/kg.

* * * * *